(12) United States Patent
Wallace et al.

(10) Patent No.: US 7,507,423 B2
(45) Date of Patent: Mar. 24, 2009

(54) EXTRACTION OF FLAVONOIDS

(75) Inventors: Robert Gerard Wallace, Willetton (AU); Willfrits Gerald Burong, Ballajura (AU)

(73) Assignee: Biorex Health Limited (AU)

( * ) Notice: Subject to any disclaimer, the term of this patent is extended or adjusted under 35 U.S.C. 154(b) by 86 days.

(21) Appl. No.: 10/169,968

(22) PCT Filed: Jan. 11, 2001

(86) PCT No.: PCT/AU01/00016

§ 371 (c)(1),
(2), (4) Date: Oct. 22, 2002

(87) PCT Pub. No.: WO01/51482

PCT Pub. Date: Jul. 19, 2001

(65) Prior Publication Data

US 2003/0147980 A1     Aug. 7, 2003

Related U.S. Application Data

(60) Provisional application No. 60/175,443, filed on Jan. 11, 2000.

(30) Foreign Application Priority Data

Jan. 11, 2000  (AU) ..................... PQ5043

(51) Int. Cl.
*A61K 36/00*     (2006.01)

(52) U.S. Cl. ................. 424/725; 424/757; 424/773; 424/774; 424/775; 424/776; 424/777; 424/778; 424/779

(58) Field of Classification Search .................. None
See application file for complete search history.

(56) References Cited

U.S. PATENT DOCUMENTS

| | | | |
|---|---|---|---|
| 4,968,787 A | 11/1990 | Inada et al. | |
| 5,320,949 A | 6/1994 | Shen | |
| 5,554,519 A | 9/1996 | Weber et al. | |
| 5,621,247 A | 4/1997 | Hirao et al. | |
| 5,763,389 A | 6/1998 | Shen et al. | |
| 5,827,682 A | 10/1998 | Bryan et al. | |
| 5,851,792 A * | 12/1998 | Shen et al. | |
| 5,936,069 A | 8/1999 | Johnson | |
| 6,083,553 A | 7/2000 | Waggle et al. | |
| 6,132,795 A * | 10/2000 | Holbrook et al. | 426/634 |
| 6,146,668 A * | 11/2000 | Kelly et al. | 426/46 |
| 2001/0010930 A1 | 8/2001 | Obata et al. | |
| 2005/0209313 A1 | 9/2005 | Wallace | |

FOREIGN PATENT DOCUMENTS

| | | |
|---|---|---|
| CN | 1136222 | 11/1996 |
| EP | 0 812 837 | 12/1997 |
| EP | 0 827 698 | 3/1998 |
| EP | 0 837 139 | 4/1998 |
| JP | 01-258669 | 10/1989 |
| JP | 10-218874 | 8/1998 |
| JP | 10-316671 | 12/1998 |
| JP | 11-089589 | 4/1999 |
| JP | 2000-256345 | 9/2000 |
| JP | 2002-50063 | 1/2002 |
| WO | WO 95/10512 | 4/1995 |
| WO | WO 95/10529 | 4/1995 |
| WO | WO 95/10530 | 4/1995 |
| WO | WO 98/49153 | 11/1998 |
| WO | WO 01/51482 | 7/2001 |

OTHER PUBLICATIONS

Dini et al. (J. Agric. Food Chem (1998), vol. 46, pp. 5089-5092).*
Derwent Abstract No. 99-458297/38 & WO 99/35138. Jan. 12, 1998.
Derwent Abstract No. 99-076456/07 & JP 10 316671. Dec. 2, 1998.
http://en.wikipedia.org/wiki/Flavonoid.
http://dictionary.reference.com/search?q=aglucone&r=66.
http://www.m-w.com/cgi-bin/dictionary?book=Dictionary&va=vegetable.
http://dictionary.reference.com/search?q=glucoside&r=66.
http://www.rpi.edu/dept/chem-eng/Biotech-Environ/DOWNSTREAM/disrupt.htm.
http://en.wikipedia.org/wiki/Hypocotyl.
Matsuura et al., 1995. *Biosci. Biotech. Biochem.*, 59:1623-1627.
T.L. Graham, 1991. *Plant Physiol.*, 95:594-603.

* cited by examiner

*Primary Examiner*—Susan C Hoffman
(74) *Attorney, Agent, or Firm*—Merchant & Gould, P.C.

(57) ABSTRACT

A method of producing an enriched flavonoid aglycone extract from starting material containing a suitable flavonoid glycoside and/or conjugate thereof comprising the steps of: (i) enzymatically converting the flavonoid glycoside or conjugate thereof into the flavonoid aglycone; (ii) adjusting the pH to render the flavonoid aglycone soluble and removing the insoluble fraction; and (iii) adjusting the pH to render the soluble flavonoid aglycone relatively insoluble and forming an extract containing the same.

38 Claims, No Drawings

EXTRACTION OF FLAVONOIDS

FIELD OF THE INVENTION

The present invention relates to a method of extracting a flavonoid aglycone from starting material containing a flavonoid glycoside and/or conjugate thereof. More particularly, the present invention provides an efficient method of producing enriched flavonoid aglycones extracts from plant material using aqueous solvents.

BACKGROUND ART

Flavonoids are a class of phytochemicals with wide ranging applications including their use as therapeutics, anti-microbials and antioxidants. They are capable of treating and or preventing a range of medical disorders and diseases including degenerative diseases such as heart disease, Alzheimer's disease, dementia and cancer, to mention a few. The characteristics and properties of flavonoids are well documented in the scientific literature.

The demand for 'natural' phytochemical remedies is increasing and will increase further as the average age of the world population steadily increases. Furthermore, the younger sections of the population are turning more to natural alternatives for treating or preventing medical conditions. In addition, there is a strong demand for such materials to be free of organic solvent residues, particularly those that are industrially synthesised, and for products produced with minimum burden to the environment. Society is also placing a high value on the use of biodegradable materials and processes that have minimal environmental impact.

The flavonoids are a sub-group of the plant polyphenols, triple ringed structures consisting of a basic fifteen carbon atoms skeleton. Plant flavonoid aglycones (i.e. flavonoids without attached sugars) occur in a variety of structural forms. However, all contain fifteen carbon atoms in their basic nucleus and these are arranged in a $C_6$-$C_3$-$C_6$ configuration, that is two aromatic rings linked by a three carbon unit which may or may not form a third ring.

The important role of flavonoids in diet and medicine is becoming more and more recognised. It is the flavonoids in red wine, green tea, extra virgin olive oil, soy products, fruit and vegetables, various traditional herbal medicines teas and tinctures that are at least partly responsible for the benefits gained from their consumption.

One group of flavonoids whose value is well established is the isoflavones. The isoflavones have a characteristic structure and form a particular isomeric class of flavonoids. The interest in isoflavones has been extensive including the suggestion that they are the factor in traditional oriental diets responsible for the lower incidence of breast and prostrate cancers in some populations of the eastern Asian region.

The isoflavones while appearing in other plant families are most strongly associated with the legumes, in particular with the Papilionoideae subfamily of the Leguminosase which includes many well known fodder crops such as clover, pulses—beans, soy beans, and peas, and shrubs such as gorse and broom.

In addition to the benefits of isoflavones to human and animal health, there has recently been shown application in the animal feeds industry where swine administered feed supplemented with isoflavones showed increased average daily weight gains, but no increase in feed intake. The pigs also had increased percentages of carcass muscle and higher estimated muscle gain per day.

While in an ideal world we would all obtain enough of these compounds from the careful selection of foods, meals and drinks, in reality especially for city workers, this is frequently just not possible. Therefore there exists a need and demand for flavonoid rich preparations that can be conveniently and effectively used as dietary supplements or therapeutics.

Prior art techniques for extracting flavonoids generally suffer from one or more of the following drawbacks: (i) they involve the use of toxic reagents (ii) they require undue multiple extractions (iii) they involve extraction of the flavonoid in its glycosylated form (flavonoid glycoside) (iv) they are too time consuming and (v) they involve the use of significant quantities of flammable organic solvents.

The present invention seeks to overcome the shortcomings of the prior art and provide a simple and convenient method for isolating flavonoids at relatively high yields compared to prior art methods.

DISCLOSURE OF THE INVENTION

The present invention provides a method of producing an enriched flavonoid aglycone extract from starting material containing a suitable flavonoid glycoside and/or conjugate thereof comprising the steps of:

(i) enzymatically converting the flavonoid glycoside or conjugate thereof into the flavonoid aglycone;

(ii) adjusting the pH to render the flavonoid aglycone soluble and removing the insoluble fraction; and (iii) adjusting the pH to render the soluble flavonoid aglycone relatively insoluble and forming an extract containing the same.

For the purposes of the present invention the term "flavonoid" is any plant polyphenol having the general structural formula:

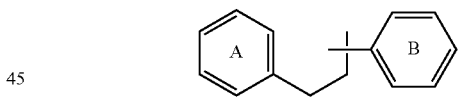

or dimers, trimers or polymers thereof.

Particular flavonoids for the purposes of the present invention include chalcones, dihydrochalones, aurones, flavanones, flavones, neoflavonoids, catechins, flavonols, dihydroflavonols, proanthocyanidins, flavans, flavan-3-ols and biflavonoids, their variously methoxylated and other modified forms such as conjugates, such as acyl conjugates and more specifically includes acacetin, apigenin, baicalein, chrysin, chrysoeriol, datiscetin, dihydrobinetin, dihydrokaempferol, diosmetin, catechin, epicatechin, eriodictyol, fisetin, fustin, galangin, hesperetin, isorhamnetin, kaempferol, luteolin/digitoflavone, morin, myricetin, naringenin, oroxylin A, ponciretin, quercetagetin, quercetin, robinetin, scutellarein, silymarin group, silybin, silidianin, silicristin, skullcapflavone II, tangeretin, wogonin, and isoflavones, such as genistein, daidzein, formononetin, biochanin A, baptenin and pratensein, having the general structural formula:

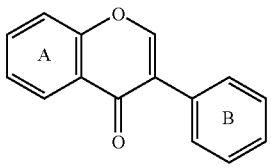

The starting material may be varied and preferably comprises plant material such as a plant or part or preparation thereof that contains a flavonoid glycoside and/or a conjugate thereof. In particular, plant material includes leaves, petals, sepals, flowers, petioles, shoots, roots, stems, seeds, pods, tubers, bark, cambium, wood, galls, fruit, vegetables, herbs, bacteria, algae, ferns, sap, resins, skins such as grape, apple, onion and avocado skins, peels including citrus peels, fruit rinds, pomace such as apple, wine marc, grain hulls, straw, hay, oil seed cakes from olives, rapeseed or canola, and other oil crop extractions. The starting material may also be genetically modified (genetically engineered) organisms such as modified bacteria, algae or fungi and GM crops and their parts and products.

One particular class of starting material are soaked and germinating seeds and sprouted seeds such as legume seeds. In legume seeds, aside from soya beans, there is essentially no isoflavonoid content in the dry seed but it is found that as they develop from soaking into sprouts definite levels of isoflavones appear and the isoflavone level in the extract and the yield on the basis of weight of the dry seeds markedly increases. This increase may continue to at least until the stage where the leaf sprout appears and the first leaves open out.

Further, the seed development and flavonoid synthesis may be affected by temperature and preferably the seed development and thus isoflavones generation is allowed to occur at about 23 to 28° C. It will be appreciated that generally speaking the yields will be higher at higher temperatures (up to an upper limit) for younger seeds and yields lower at lower temperatures for the same aged seeds due to the well recognised effect of temperature on germination.

Applicant has also found that with pre-sprouting soya beans may be used as a starting material to generate a sufficiently enriched flavonoid product. In this regard, soya beans contain significant levels of isoflavonoid glycosides in the dry seed. However, soaking and germination may be conducted to generate the enzymes required to convert the glycosides to aglycones. In this regard, the soya beans are preferable soaked for at least on day at about room temperature (25° C.) to activate endogenous enzymes and thus to increase the isoflavonoid level in the extract obtained according to the invention. The higher levels of enzymes necessary to produce the aglucones may coincide with the development of the root beneath the seed coat. Again the onset of the better levels of isoflavonoids in the extracts and yield per seed will be temperature dependent.

Extraction of such seeds and sprouts can yield what can be described as (iso)flavonoid enriched protein extracts of 50 to 60% or higher protein contents. These enriched protein concentrates can be converted into (iso)flavonoid protein isolates by washing out of water soluble carbohydrates etc to raise the protein level. Yield may be further improved by increasing the fineness of crushing of the germinating seeds and sprouts, this is particularly so when the starting material is particularly robust.

Plants for the purposes of the present invention include any plant containing a flavonoid glycoside and/or conjugate thereof, however, particularly preferred plants are legumes such as soy, chickpeas (*Cicer* spp such as *Cicer arietinum*), white sweet clover (*Meliotus alba*), lucerne or alfalfa (*Medicago sativa*) or *Trifolium* species. It will be appreciated that a combination of material from different plants may constitute the starting material.

Preferably, the conversion of the flavonoid glycoside and/or conjugate thereof is complete. However, it is more likely and practical that a portion of the flavonoid glycoside and/or conjugates thereof in the starting material will not be converted to flavonoid aglycones. Clearly, the higher the degree of conversion, the more flavonoid aglycones that will be recovered from the extraction process. In any event the level of conversion achieved in the method of the invention will be determined by the operating parameters, including the required output of the process.

The enzymes used to convert the flavonoid glycoside may be varied and include enzymes with the ability to hydrolyse glycoside bonds such as an enzyme from the group comprising glycosidases, β-glycosidases, β-galactosidase, β-glucuronidase, pectinases, hesperidinase, anthocyanase, rhamnodiastase, naringinase or takadiastase.

Other enzymes include those adapted to hydrolyse the bond in the flavonoid glycoside conjugates between the glucose (sugar) moiety and the conjugated moiety (for example an acyl group) such as the isoflavone 7-0-glycoside-6" malonate malonylesterase or equivalent enzymes that may be found in suitable plants.

Such enzymes can be obtained commercially or from sources apparent to one skilled in the art including animals such as from pig livers, plants such as *Trifolium* spp, *Cicer* spp, *Helianthus* spp, *Melilotus* spp, *Medicago* spp, *Camellia* (Thea) *sinensis*, *Prunus* spp, (eg *P. amygdalus*, *P. communis*, *P. avium*, *P. armeniaca*), *Rhamnus frangula*, and *Rhamnus utilis*, fungi such as *Aspergillus* spp including *Aspergillus niger* or *Aspergillus oryzae*, *Saccharopolyspora erythraea*, *Robinia pseudoacacia L* and *Rhizobium* spp, bacteria such as *Leuconostoc oenos*, *Pediococcus cerevisiae* and *Lactobacillus plantarum* or intestinal bacteria such as *Bacteriodes* spp and yeasts such as *Saccharomyces cerevisiae*, *Hansenula anomala*, *Kloeckera apiculata* and *Candida pulcherimma*.

The present invention also extends to the use of genetically engineered enzymes such as those obtained from genetically modified (genetically engineered) organisms. In this regard, using genetic manipulation, plants or micro-organisms which would otherwise produce insufficient amounts of enzymes or enzymes with insufficient activity could be utilized. Furthermore, genetic engineering can also be used to improve the characteristics of enzymes such as their activity. All such genetically engineered products are capable of being used in the method of the present invention.

Depending on the circumstances, the enzymatic conversion of the flavonoid glycoside or conjugate thereof to the flavonoid aglycone may involve the use of a plurality of enzymes that may be used simultaneously or sequentially to achieve the necessary conversion. One of ordinary skill in the art is able to determine the nature of the enzymatic conversion based at least on the requirements of the process and the starting material.

In some instances the conversion of the flavonoid glycoside and/or conjugate thereof to the flavonoid aglycone may require treatment with a plurality of enzymes, used in sequence or simultaneously. In this regard, the flavonoid glycoside and/or conjugate thereof may require conversion to an intermediate form of compound or compounds before conversion to the flavonoid aglycone. The requirement for conversion to an intermediate and the particular enzymes used will be apparent to one skilled in the art. For example, narangin (a glycoside) must first be converted to prunin (intermediate glycoside) using alpha-rhamnosidase, and then to its flavonoid aglycone form naringinin by the hydrolysis of glucose moieties using a β glucosidase.

The flavonoid glycoside may also be pretreated to remove one or more sugar residues, or portions thereof, prior to enzymatic conversion to the flavonoid aglycone. In this regard, the flavonoid glycoside may be treated to hydrolyse some of the sugar residues, or portions thereof such as saccharide units, to yield a partially converted flavonoid glycoside. In this option, one or more sugar residues may be removed from the flavonoid glycoside by hydrolysis using strong acids that leave at least one sugar residue on the flavonoid glycoside.

Other variables may need to be adjusted to achieve the optimum performance from a given extraction process and more particularly the enzymatic conversion. The control of these variables and the particular combination of conditions that will result in the best conversion is readily apparent to one skilled in the art. Such variables include temperature, moisture content and addition of other solutes or enzyme stabilizing agents.

When the starting material is plant material with a relatively intact cellular structure containing the flavonoid glycoside and/or conjugate thereof and the enzyme, the flavonoid glycoside and/or conjugate thereof is generally separated intracellularly from the enzyme adapted to convert it to the flavonoid aglycone. In this situation, the enzyme and the flavonoid glycoside and/or conjugate thereof may be contacted by at least disrupting the cellular structure of the plant material.

Thus, the present invention also provides a method of producing an enriched flavonoid aglycone extract from plant material containing a flavonoid glycoside and/or conjugate thereof comprising the steps of:

(i) disrupting the cellular structure of the plant material to contact the flavonoid glycoside or conjugate thereof contained therein with at least one enzyme contained therein adapted to convert the flavonoid glycoside or conjugate thereof to a flavonoid aglycone and thus converting the flavonoid glycoside or conjugate thereof into the flavonoid aglycone;

(ii) adjusting the pH to render the flavonoid aglycone soluble and separating off the insoluble fraction; and (iii) adjusting the pH to render the flavonoid aglycone relatively insoluble and isolating the flavonoid aglycone.

Treatments to at least disrupt the cellular structure include treatments that rupture the cells and are varied and readily apparent to one skilled in the art. They include treatments such as grinding, crushing, pounding or rolling, freezing and thawing, enzyme treatments such as hemicellulases or cellulases, ultrasonics, drying, exposure to ultra violet light, use of pressure reduction or elevation including both extrusion and sealed batch pressure applications, microbial digestion or ensilagation, exposure to oxidising and other chemicals, detergents treatments or any combination of the foregoing.

It will be appreciated that any components used in the disruption process, that would hinder the remainder of the process should be removed from the reaction mix prior to further processing.

It will also be appreciated that extracts produced according to the method of the present invention may be treated further to further increase the concentration of the flavonoids of interest. In this regard, additional purification protocols may be carried out such as alcohol leaching. In this regard, it has been found that by exposing the extracts of the present invention to an alcohol (e.g. methanol, ethanol or aqueous ethanol) leach and evaporating the solvent, significant concentration enrichment of the flavonoid aglucones of about 2-6 fold may be obtained.

As indicated above, the enzyme and the flavonoid glycoside and/or conjugate thereof may both be contained within the starting material. However, the starting material may comprise the flavonoid glycoside and/or conjugate thereof with an insufficient amount of enzyme or even no enzyme to perform the necessary conversion. In such instances, the method of the invention may further comprise the addition of an enzyme adapted to convert the flavonoid glycoside and/or conjugate thereof into the flavonoid aglycone.

Thus, the present invention also provides a method of extracting a flavonoid aglycone from starting material containing a flavonoid glycoside and/or conjugate thereof comprising the steps of:

(i) converting the flavonoid glycoside and/or conjugate thereof into the flavonoid aglycone by adding an enzyme adapted to convert the flavonoid glycoside and/or conjugate thereof into the flavonoid aglycone to the starting material;

(ii) adjusting the pH to render the flavonoid aglycone soluble and separating off the insoluble fraction; and (iii) adjusting the pH to render the flavonoid aglycone relatively insoluble and isolating the flavonoid aglycone from solution.

Once the flavonoid aglycone has been produced it may be necessary to protect it from polymerisation or other unwanted modification. For example, polyphenol oxidase activity may need to be limited or removed to prevent polymerisation of the flavonoid aglycone. This may be achieved by physical means eg heat, or chemical means eg sulphur dioxide, sodium metabisulphite, hydrocyanic acid, carbon monoxide, protein digesting enzyme or enzymes; and/or by the use of methods to exclude oxygen, e.g. by providing an atmosphere of carbon dioxide, or nitrogen, or by vacuum suction. In the latter approach the exclusion of oxygen being maintained until the polyphenol oxidase activity can be conventionally permanently eliminated or alternatively until the flavonoid aglycone has been separated from the liquid or solids containing the polyphenol oxidase enzyme.

The pH is adjusted to render the flavonoid aglycone soluble. Thus, the pH may be adjusted to approximately at least 8.5 and more preferably at least 9.6, 11 or 12 or alternatively to approximately 9.6-12. However, the particular level of pH adjustment required will vary depending at least on the particular flavonoid aglycone being extracted.

The efficiency of the alkaline extraction effect in the method of the present invention is surprising as the extraction yield increases as the pH is raised beyond the pH value where there is effectively 100% (99.9%) ionisation of the isoflavonoids (when pH=pKa+3 pH units or about 10.2), at this pH value the isoflavonoid aglycones are completely water soluble. The extraction continues to increase even at pH's which are expected to cause breakdown of the isoflavones at pH 12-12.5

Furthermore, the yield would be predicted not to increase as the pH is raised above that which gives complete ionisation (pKa+3) but rather to decrease due to increased rates of base catalysed oxidisation. Genistein and biochanin A have been found to have pKa's of approximately 7.2. This would parallel the observed effect of changing the acid precipitation pH, no change in yield is seen over a thousand fold variation in proton ion concentration once the genistein and biochanin A isoflavonoid aglycones are effectively completely (99+%) uncharged.

The adjustment of the pH to render the flavonoid aglycone soluble may be achieved in any one of a number of ways apparent to one skilled in the art including the addition of an alkali such as sodium hydroxide, potassium hydroxide, calcium hydroxide, other alkali metal and alkali earth metal hydroxides or sodium acetate, which may be in a liquid or solid form, or ammonia gas. The pH is altered to ensure a sufficient proportion of the flavonoid aglycone is solubilised. Plant material remaining insoluble may be treated further to achieve a more complete extraction of the flavonoid aglycone into the liquid phase. Such further treatments include washing, rinsing and percolating the insoluble plant material.

Once the flavonoid aglycone is sufficiently solubilised, the insoluble fraction may be removed by any one or a combination of routine methods apparent to one skilled in the art for separating soluble and insoluble fractions. Such methods include: settling, filtration and centrifugation. It will appreciated that for the purposes of the present invention the phrase "separating off the insoluble fraction" and obvious variants thereof encompasses the removal of a portion of the insoluble fraction and more particularly includes removal of the majority of the insoluble fraction which may be achieved via centrifugation or other readily apparent means.

Preferably, the alkaline extraction is conducted with minimal aeration of the reaction volume to avoid breakdown of the flavonoids. In this regard, it has been surprisingly found that minimising aeration of reaction volume during the alkaline extraction significantly enhances the yield. The aeration may be minimised during the alkaline extraction in a variety of ways including but not limited to avoiding agitation of the sample, splashing, vigorous stirring, other mixing of air with the liquid sample. Alternatively, to prevent aeration the alkaline extraction may be carried out under an oxygen reduced or oxygen free atmosphere such as under an atmosphere of nitrogen or argon or oxygen absorbing compounds maybe incorporated into the alkaline solution.

The pH is then adjusted to render the flavonoid aglycone insoluble. Thus, the pH may be adjusted to approximately 2 or 3, or 2-6 or more preferably approximately 3-5.6 such as 3.5, 3.6, 5,3 or 5.6. However, the particular level of pH adjustment required will vary depending at least on the particular flavonoid aglycone being extracted. The optimum pH for this stage of the method may be determined routinely by a person of ordinary skill who may undertake empirical trials to determine the optimum pH for a given flavonoid aglycone.

The adjustment of the pH to render the flavonoid aglycone insoluble may be achieved in any one of a number of ways apparent to one skilled in the art including the addition of an acid such as hydrochloric acid, sulphuric acid, phosphoric acid, nitric acid, lactic acid, tartaric acid, citric acid, acetic acid, or propionic acid, which may be in liquid, solid or gaseous form. The pH is altered to ensure a sufficient proportion of the flavonoid aglycone is rendered insoluble. If required, the pH adjustment can be conducted with agitation to ensure thorough mixing of the reactants and the most practically complete acidification of the flavonoid aglycones possible. The soluble fraction may be treated to further to achieve a more complete transfer of the flavonoid aglycone into the insoluble phase.

Once the flavonoid aglycone is sufficiently separated as a suspension or a precipitate, the insoluble fraction may be removed by any one or a combination of routine methods apparent to one skilled in the art for separating soluble and insoluble fractions. Such methods include: settling, filtration, crystallisation, co-crystallisation and centrifugation. Salt may also be added to aid the separation and the reaction mix may be concentrated by evaporation or partial freezing, as required. It may also be of assistance to the separation to reduce the temperature or chill the reaction volume.

The separation may also be achieved by other conventional techniques such as the use of organic solvents, selective membrane filtration and chromatography including thin layer chromatography, liquid chromatography and high pressure liquid chromatography. Acidified aqueous or aqueous organic preparations of the reaction mix may also be purified or concentrated by absorbing them onto charcoal.

A further approach to purification would be to dissolve the precipitate from the acid extraction step into a suitable solvent and then modify the solution so that one or more of the nonflavonoid components become insoluble and precipitate out, a suitable procedure for this would be to dissolve the precipitate into ethanol and then modify by adding acetone, any co-dissolved sugars, saponins and proteins would then be expected to precipitate out to a greater or lesser extent. The remaining solution can be evaporated and the concentrated extract recovered or the solution may be further processed.

One potential complication of using plant material as the starting material for the extraction is the co-precipitation of unwanted plant proteins during the extraction. In this regard, the various conditions manipulated during the extraction to separate the flavonoid aglycone may not adequately separate it from other plant proteins. This may be addressed by additional treatment steps applied to the starting material or during the extraction process to at least decrease the problems associated with co-precipitation.

Thus, the present invention may further comprise a treatment in which the unwanted proteins are modified so that they do not unduly interfere with the extraction of the flavonoid aglycone in the method of the present invention. Such treatments include those that achieve: (i) a reduced level of unwanted proteins in the soluble phase after the alkalisation step and (ii) an increased level of unwanted proteins or protein material in the soluble phase after the acidification step.

The treatments may be varied and include those readily apparent to one of ordinary skill. Treatments encompassed by the present invention include: heating, chemical treatment eg with tannin or bentonite, enzyme treatment or electrical discharge of the starting plant material before the alkaline pH adjustment or the reaction mix resulting from the alkaline extraction step to insure that the unwanted proteins are in an insoluble form which can be separated from the soluble flavonoid aglycone of interest. A further approach would be to pass the reaction mix resulting from the alkaline extraction step through a column packed with a material that absorbs protein.

Alternatively, the reaction mix resulting from the acid extraction step may be treated with a proteinase such as pepsin or papain that converts the unwanted proteins to forms soluble in acidic media. Size exclusion chromatography may also be used including gel filtration or a size exclusion membrane filter with pores small enough to permit flavonoid molecules but not the larger proteins through could be employed. Other biological means may also be used including fermentation with protein digesting or absorbing microbes. Ensilagation of the crushed material may also assist in the extraction protocol.

As indicated previously the method of the present invention provides for relatively high yields of flavonoids such as isoflavonoids. For example, yields may be at least approximately 25% higher than methods employing an equivalent process but using organic solvents to extract, more preferably at least 50% higher and even more preferably at least 67% higher than published yields.

EXAMPLES

Unless indicated to the contrary: (i) the cloth filtrate from the alkaline extractions in the examples hereunder was rinsed twice with a solution of pH equivalent to the solution used for the extraction; (ii) all alkaline extractions in the examples hereunder were carried out with minimal aeration and according to the following general methodology: (a) the plant material was dispersed with a larger quantity of water, usually at least twice to four times greater (b) to the solution-suspension was added initially small volumes of concentrated sodium hydroxide solution (approximately 5M), (c) later as the selected pH value was approached the sodium hydroxide solution was added drop-wise, (d) the sodium hydroxide was mixed efficiently with the solution-suspension (minimal aeration) and time allowed for the mixture to come to a steady pH value (d) after the final attainment of the desired pH, the value was checked after a further 2 to 5 minutes and the pH adjusted in the event of a drift in the value having occurred; and (iii) all flavonoid yields referred to in the examples were determined using thin layer chromatography or by UV spectrographic methods.

Example 1A

A sample of approximately 1 kg of leaves on (long) stems of subterranean clover (*Trifolium subterraneum L.*) grown in the South West of Western Australia over the 1999 winter, was collected in early October, stored for ca 20° C. for one day and 5° C. for 10 days. The leaves of approximately 0.5 kg of this stored material were cut off and retained in a plastic bag.

25 g of the clover leaves were mixed with 50 g of acid washed wet white sand and ground in a mortar and pestle for 3.5 minutes. The ground leaf and sand material was transferred to a sealed plastic bag and 10 minutes was heat treated at approximately 62° C. for 20 minutes.

Next day the heat treated material was transferred to a beaker and 200 mL of deionised water added, with stirring 5M sodium hydroxide solution was added from a dropper to raise the pH of the suspension to pH 9.6. The coarse fibrous material was removed by passing the suspension through a triple layer of fine gauze, the sludge like material that passed through the gauze was removed by centrifuging at 2,000 rpm for 2 minutes.

The pH of the separated solution was then adjusted to 5.3. The pH 5.3 mixture was kept at approximately 1° C. for 48 hours and then concentrated by partial freezing of the solution and separation of the ice formed so the final volume was approximately 100 mL, the remaining solution and the precipitate was filtered through filter paper.

The filter paper and retained precipitate was dried at 40° C. and the isoflavone contents measured in a modified, that is no grinding version, of the method of C. M. Francis and A. J. Millington, ('Varietal variation in the isoflavone content of subterranean clover: its estimation by a microtechnique', C. M. Francis and A. J. Millington, *Australian Journal of Agricultural Research*, volume 16, pages 557-64, 1965).

The weight of the material retained on filter paper was calculated by measuring the weight of four filter papers calculating the average weight and subtracting this average weight from the measured weight of the experimentally used filter paper and its retained material.

Results

Weight of retained material on the filter paper—0.35g. Level of isoflavones in the dry filtered precipitate was Genistein 26.1 g/100 g, Biochanin A 8.5 g/100 g, Formononetin 2.1 g/100 g, Daidzein not detected. The calculated extraction of isoflavones from 25 g of clover leaf was 0.128 g.

Example 1B

A sample of approximately 1 kg of leaves on (long) stems of subterranean clover (*Trifolium subterraneum L.*) of the cultivar Trikkala grown in the South West of Western Australia over the 1999 winter, was collected in early October, stored at ca 20° C. for one day and 5° C. for 10 days.

The leaves of approximately 0.5 kg of this stored material were cut off and retained in a plastic bag. 25 g of the clover leaves were mixed with 50 g of acid washed wet white sand and ground in a mortar and pestle for 3.5 minutes. The ground leaf and sand material was transferred to a sealed plastic bag for 10 minutes and then was heat treated at approximately 62° C. for 20 minutes.

Next day the heat treated material was transferred to a beaker and 200 mL of deionised water added, with stirring 5M sodium hydroxide solution was added from a dropper to raise the pH of the suspension to pH 12.0. The coarse fibrous material was removed by passing the suspension through a triple layer of fine gauze.

The pH of the separated solution and suspension was then adjusted to 5.6. The pH 5.6 mixture was kept at approximately 1° C. for 48 hours and then concentrated by partial freezing of the solution and separation of the ice formed so the final volume was approximately 100 mL, the remaining solution and the precipitate was filtered through filter paper. The filter paper and retained precipitate was dried at 40° C. and the isoflavone contents measured as in example 1A.

The weight of the material retained on filter paper was calculated by measuring the weight of four filter papers calculating the average weight and subtracting this average weight from the measured weight of the experimentally used filter paper and its retained material.

Results

Weight of retained material on the filter paper —1.1 g. Level of isoflavones in the dry filtered precipitate was Genistein 7.3 g/100 g, Biochanin A 2.4 g/100 g, Formononetin 0.55 g/100 g, Daidzein not detected. The calculated extraction of isoflavones from 25 g of clover leaf was 0.113 g.

Example 1C

A sample of approximately 1 kg of leaves on (long) stems of subterranean clover (*Trifolium subterraneum L.*) of the cultivar Trikkala grown in the South West of Western Australia over the 1999 winter, was collected in early October, stored at ca 20° C. for 1 day and 5° C. for 10 days. The leaves of approximately 0.5 kg of this stored material were cut off and retained in a plastic bag.

26 g of the clover leaves were mixed with 52 g of acid washed wet white sand and ground in a mortar and pestle for 3.5 minutes. The ground leaf and sand material was transferred to a sealed plastic bag for 10 minutes and then was heat treated at approximately 62° C. for 20 minutes.

Next day the heat treated material was transferred to a beaker and 200 mL of deionised water added, with stirring 5M sodium hydroxide solution was added from a dropper to raise the pH of the suspension to pH 12.0. The coarse fibrous material was removed by passing the suspension through a triple layer of fine gauze. The pH of the separated solution and suspension was then adjusted to 3.5. The pH 3.5 mixture was kept at approximately 1° C. for 48 hours and then concentrated by partial freezing of the solution and separation of the ice formed so the final volume as approximately 100 mL, the remaining solution and the precipitate was filtered through filter paper. The filter paper and retained precipitate was dried at 40° C. and the isoflavone contents measured as in example 1A.

The weight of the material retained on filter paper was calculated by measuring the weight of four filter papers calculating the average weight and subtracting this average weight from the measured weight of the experimentally used filter paper and its retained material.

Results

Weight of retained material on the filter paper—1.09 g. Level of isoflavones in the dry filtered precipitate was Genistein 11.1 g/100 g, Biochanin A 3.8 g/100 g, Formononetin 0.85 g/100 g, Daidzein not detected. The calculated extraction of isoflavones from 26 g of clover leaf was 0.171 g.

In contrast, using the same protocol and equivalent starting material but exposing the alkaline extraction product to an additional filtration step through sintered glass yields were— weight of retained material on the filter paper—0.415 g, genistein 6.3 g/100 g, Biochanin A 1.25 g/100 g, Formononetin 0.40 g/100 g. The calculated extraction of isoflavones from 26 g of clover leaf was 0.033 g.

Example 1D

A sample of approximately one kilogram of leaves on (long) stems of subterranean clover (*Trifolium subterraneum* L.) of the cultivar Trikkala grown in the South West of Western Australia over the 1999 winter was collected in early October, stored for ca 20° C. for one day and 5° C. for 10 days. The leaves of approximately 0.5 kg of this stored material were cut off and retained in a plastic bag.

26 g of the clover leaves were mixed with 52 g of acid washed wet white sand and ground in a mortar and pestle for 3.5 minutes. The ground leaf and sand material was transferred to a sealed plastic bag for 10 minutes and then was heat treated at approximately 62° C. for 20 minutes.

Next day the heat treated material was transferred to a beaker and 150 mL of deionised water added, with stirring 5M sodium hydroxide solution was added from a dropper to raise the pH of the suspension to pH 11.0. The coarse fibrous material was removed by passing the suspension through a triple layer of fine gauze. Part of the sludge that appeared in the alkaline clover suspensions was allowed to settle and separated by pouring the liquid with the remaining suspended material off into another beaker.

The pH of the separated solution and suspension was then adjusted to 3.6. The pH 3.6 mixture was kept at approximately 1° C. for 48 hours and then concentrated by partial freezing of the solution and separation of the ice formed so the final volume as approximately 100 mL, the remaining solution and the precipitate was filtered through filter paper. The filter paper and retained precipitate was dried at 40° C. and the isoflavone contents measured as in example 1A.

The weight of the material retained on filter paper was calculated by measuring the weight of four filter papers calculating the average weight and subtracting this average weight from the measured weight of the experimentally used filter paper and its retained material.

Results

Weight of retained material on the filter paper —1.25 g. Level of isoflavones in the dry filtered precipitate was Genistein 15.5 g/100 g, Biochanin A 5.2 g/100 g, Formononetin 1.30 g/100 g, Daidzein not detected. The calculated extraction of isoflavones from 26 g of clover leaf was 0.125 g.

The ratio of the isoflavones in the precipitates of examples 1A to 1D are respectively Genistein 10, 10, 10, 10 to Biochanin A, 3.2, 3.3, 3.4, 3.4 to Formononetin 0.8, 0.8, 0.8, 0.8, thus indicating that the ionisation equilibriums are likely to be very similar and are probably involve the 7 position phenol OH group shared by all three.

Example 1E

Subterranean clover leaves were cut from late (post start of flowering) field grown mixed Trikkala and Larisa subterranean clover plants, which had been stored at approximately 5° C. for a month. The attached petiole lengths were 1 to 1.5 cm long.

10 g portions were ground for approximately 70 seconds, and after five minutes sodium metabisulphite was solution was added to preserve the material, final concentration being 1.2% of the leaf weight. The plant material was stored frozen until extraction when the individual samples were mixed with water and the pH adjusted to the selected value, after two hours they were cloth filtered, the filtered solid material rinsed twice, the filtered solution adjusted to pH 2 and stored at 20° C. overnight before being paper filtered on paper and the filtered material warm dried.

Results

The results are set out hereunder in Table 1.

TABLE 1

| Sample | Alkaline extraction (pH) | Yield[A] (isoflavones) | Yield[B] (isoflavones) |
|---|---|---|---|
| A | 9 | 0.35g | 11.9 |
| B | 10 | 0.45g | 13.9 |
| C | 11 | 0.48 | 13.2 |
| E | 12 | 0.56 | 13.6 |
| F | 12.5 | 0.68 | 10.6 |

[A]amount of isoflavones per 100 g of leaf material
[B]isoflavones content in precipitate g/100 g Example 1F The same leaf material as in example 1 E was processed as in example 1 E with the addition steps of being heated at 58 to 64° C. for forty minutes before being extracted at pH 10 or pH 12.

Results

The results are set out hereunder in Table 2.

TABLE 2

| Sample | Alkaline extraction (pH) | Yield[A] (isoflavones) | Yield[B] (isoflavones) |
|---|---|---|---|
| A | 10 | 0.46g | 19.2 |
| B | 12 | 0.77g | 19.5 |

[A]amount of isoflavones per 100 g of leaf material
[B]isoflavones content in precipitate g/100 g

Example 1G

Subterranean clover leaves were cut from tray grown late season Trikkala subterranean clover plants that just started flowering. The proportion of leaflets to petioles was 77.5% to 22.5%.

Four batches of 11 g of leaves were prepared, each batch was ground with about 4 g of clean silica sand for 90 seconds in a mortar and pestle, then after a period of approximately 3.5 minutes a sodium metabisulphite solution was added (final concentration of 0.2% of the clover weight) was added to preserve the material, the batches were placed in individual plastic bags and heated to between 58 and 63° C. for forty minutes with a hot water bath.

The next day the individual batches were combined, deionised water (about 300 mls) added and extracted at pH 12 for approximately 20 minutes before being coarse filtered through cloth, the filtered solid material rinsed twice and the alkaline solution divided into four equal portions of 77.5 mls and each centrifuged for three and a half minutes. The individual centrifuged solutions were adjusted to pH 2.0, 3.0, 4.0 and 5.0, before being stored overnight and filtered through paper the next day. The filtered material being warm dried.

Results

The results are set out in Table 3 hereunder.

TABLE 3

| Sample | Acid extraction (pH) | Yield$^A$ (isoflavones) | Yield$^B$ (isoflavones) |
|---|---|---|---|
| A | 2 | 0.89g | 33.2 |
| B | 3 | 0.90g | 36.2 |
| C | 4 | 0.85g | 33.8 |
| D | 5 | 0.84g | 33.2 |

$^A$amount of isoflavones per 100 g of leaf material
$^B$isoflavones content in precipitate g/100 g

Example 1H

Subterranean clover leaf material was cut from late (post start of flowering) field grown mixed Trikkala and Larisa subterranean clover plants, which had been stored at approximately 5° C. for three days.

11 g portions were ground for approximately 90 seconds, and after 5 minutes mixed with water, and the pH of the mixture adjusted to pH 10, after different lengths of time, they were cloth filtered, the filtered solid material rinsed twice, the filtered solution adjusted to pH 2 and stored at 20° C. overnight before being paper filtered on paper and the filtered material warm dried.

Results

The results are set out hereunder in Table 4

TABLE 4

| Sample | Alkaline extraction time (minutes) | Yield$^A$ (isoflavones) | Yield$^B$ (isoflavones) |
|---|---|---|---|
| A | 7 | 0.46g | 6.26 |
| B | 14 | 0.53g | 7 |
| C | 60 | 0.48g | 6.6 |

$^A$amount of isoflavones per 100 g of leaf material
$^B$isoflavones content in precipitate g/100 g

Example 1I

Subterranean clover leaflets were cut from late (post start of flowering) field grown mixed Trikkala and Larisa subterranean clover plants, which had been stored at approximately 5° C. for 16 days.

10 g portions were ground for approximately 70 seconds, and after 5 minutes sodium metabisulphite was solution was added to preserve the material, final concentration being between 0 and 2.0% of the leaf weight. The plant material was stored at room temperature for 5 days before extraction when the individual samples were mixed with water and the pH adjusted to pH 10 for an 1.5 hours, then they were cloth filtered, the filtered solid material rinsed twice, the filtered solution adjusted to pH 2 and stored at 20° C. overnight before being paper filtered on paper and the filtered material warm dried.

Results

The results are contained in Table 5 hereunder.

TABLE 5

| Sample | % of sodium metabisulphite | Yield$^A$ (isoflavones) | Yield$^B$ (isoflavones) |
|---|---|---|---|
| A | 0 | 0.565 | 13 |
| B | 0.4 | 0.74 | 13 |
| C | 0.8 | 0.87 | 19.1 |
| D | 1.2 | 0.93 | 16.7 |
| E | 1.6 | 0.81 | 15.8 |
| F | 2.0 | 0.89 | 15.3 |

$^A$amount of isoflavones per 100 g of leaf material
$^B$isoflavones content in precipitate g/100 g

Example 1J

Subterranean clover leaflets were cut from late (post start of flowering) field grown mixed Trikkala and Larisa subterranean clover plants, which had been stored at approximately 5° C. for 25 days.

16 g portions were ground for approximately 90 seconds, and after five minutes sodium metabisulphite solution was added to preserve the material, final concentration being 0.2 or 1.2% of the leaf weight. The material was heated at 59 to 64° C. for 40 minutes. The sample was mixed with water and the pH adjusted to 12 for an hour and a half, then cloth filtered, the filtered solid material rinsed twice, the filtered solution centrifuged and adjusted to pH 2 and stored at 20° C. overnight before being paper filtered on paper and the filtered material warm dried.

Results

From 16 g of leaflets preserved with 0.2% sodium metabisulphite, 0.502 g dry precipitate was obtained with an isoflavone content of about 24.3 g/100 g, or about 0.76 g/100 g of leaf material, or 4.1% on a dry weight basis.

From 16 g of leaflets preserved with 1.2% sodium metabisulphite, 0.710 g dry precipitate was obtained with an isoflavone content of about 24.0 g/100 g, or about 1.07 g/100 g of leaf material, or 5.66% on a dry weight basis.

Example 1K

Subterranean clover leaflets were cut from late (post start of flowering)field grown mixed Trikkala and Larisa subterranean clover plants, which had been stored at approximately 5° C. for 25 days.

A 16 g portion was ground for approximately 90 seconds, and after five minutes sodium metabisulphite solution was added to preserve the material, final concentration being 1.2% of the leaf weight. The sample was mixed with water and the pH adjusted to 10 for an hour and a half, then cloth filtered, the filtered solid material rinsed twice, and the filtered solution adjusted to pH 2 and stored at 20° C. overnight before being paper filtered on paper and the filtered material warm dried.

Results

From 16 g of leaflets extracted at pH 10, 1.10 g dry precipitate was obtained with an isoflavone content of about 12.6 g/100 g, or about 0.86 g/100 g of leaf material, or 4.57% on a dry weight basis.

Example 2A (1) Bitter White Italian Lupines (Lupinus albus), were soaked for a day under tap water, with two changes of water. The lupines were allowed to sprout at a room temperature of approximately 25° C. and on the tenth day when the roots were well developed and at the stage the first leaves were emerging from between the opening two halves of the cotyledons 56 g lots of the sprouted lupines were ground with sand in a mortar and pestle.
(2) The ground material from (1) was left for varying time periods (16 minutes to five hours—see below) to permit the hydrolysis of the genistein glycosides present.
(3) The hydrolysed ground material was made up to approximately 300 mL with water to form a mixed solution-suspension and the pH adjusted to pH 12.0, and maintained between pH 11.9 and 12.0 at 30° C. for a given time (see below).
(4) The mixture from (3) was filtered through a cloth and centrifuged at about 600-100 rpm for five minutes in a clements model B universal centrifuge.
(5) The filtered solution from (4) was adjusted to pH 2.0 and the acidified solution was left overnight to allow the precipitate formed to settle and then filtered and dried.

Results

The results are set out in Table 6 hereunder.

TABLE 6

| Sample | Hydrolysis Time | Alkaline extraction (pH/time) | Yield$^A$ (genistein) |
|---|---|---|---|
| A | 16 minutes | 12/31 minutes | 1.8 g/100 g of dried precipitate<br>400 mg/100 g of dried seed weight |
| B | 49 minutes | 12/35 minutes | 1.81 g per 100 g of the dried precipitate<br>338 mg/100 g of dried seed weight |
| C | 100 minutes | 12/35 minutes | 1.8 g per 100 g of the dried precipitate<br>337 mg/100 g of dried seed weight. |
| D | 5 hours | 12.1/40 minutes | 1.9 g per 100 g of the dried precipitate<br>346 mg/100 g of dried seed weight |

$^A$methyl alcohol leachable genistein content

The combined dried precipitates were measured as having approximately 6% moisture, with 59% protein, 4.2% ash and 17.8% hexane extractables on a dry weight basis.

Example 2B

Lupinus albus seeds were soaked for 24 hours and then left for varying periods (23 hours, 4 days and 5 days) before grinding, waiting for 1-1.5 hours and then extracting the coarse paste at pH 10.5 for 1.25 hours. The resulting mixtures were cloth filtered to remove the precipitate and then acidified to pH 3.5 and stored before filtration through paper to isolate the acid precipitate.

Results

The results of the extraction are set out hereunder in Table 7:

TABLE 7

| Sample | Hydrolysis Time | Yield$^A$ genistein | Yield$^B$ genistein |
|---|---|---|---|
| A | 23 hours | Trace | — |
| B | 4 days | 110 mg/100 g | 0.56 |
| C | 5 days | 208 mg/100 g$^C$ | 1.12 |

$^A$amount of genistein/amount of dry seed starting material
$^B$content in precipitate g/100 g
$^C$The concentration of genistein in the methanol leachate calculated as 6.4 g/100 g.

Example 2C

White Italian lupines were soaked for twenty four hours with two one hour air breaks (at approximately 8 hours and 20 hours) and then soaked for approximately one hour every twelve hours thereafter over varying periods (12 hours-9 days). The soaked seeds were then ground with a small quantity of sand in a mortar and pestle for about ten minutes and stored in sealed beakers for varying lengths of time (65 minutes-145 minutes) before being extracted at pH 10-12, coarse filtered through a double layer of cloth, acidified (pH 2-3.5) and stored overnight before filtration through paper.

Results

The results are set out in Table 8 hereunder.

TABLE 8

| Sample | # of additional soaks | Hydrolysis time (minutes) | Alkaline extraction (pH/time) | Acid extraction (pH) | Yield$^A$ | Yield$^B$ |
|---|---|---|---|---|---|---|
| A | 1 | 65 | 12/2 hours | 2 | Trace | — |

TABLE 8-continued

| Sample | # of additional soaks | Hydrolysis time (minutes) | Alkaline extraction (pH/time) | Acid extraction (pH) | Yield[A] | Yield[B] |
|---|---|---|---|---|---|---|
| B | 1 | 65 | 12/2 hours | 3.5 | Trace | — |
| C | 3 | 110 | 12/78 minutes | 3.5 | 41 mg | 0.153 |
| D | 5 | 145 | 10/4.5 hours | 3.5 | 50 mg | 0.35 |
| E | 7 | 145 | 12/4.5 hours | 2 | 73 mg | 0.33 |
| F | 7 | 145 | 12/4.5 hours | 3.5 | 94 mg | 0.35 |
| G | 9 | 80 | 12/110 minutes | 2 | 96 mg | 0.33 |
| H | 9 | 75 | 12/75 minutes | 3.5 | 106 mg | 0.34 |
| K | 11 | 80 | 12/3.25 hours | 3.5 | 129 mg | 0.40 |
| L | 11 | 60 | 12/205 minutes | 3.5 | 129 mg | 0.41 |
| M | 18 | 95 | 12/205 minutes | 3.5 | 160 mg | 0.65 |
| N | 17 | 68 | 12/5.25 hours | 2 | 181 mg | 0.93 |

[A] genistein per 100 g of dried seed
[B] content in precipitate g/100 g

Example 2D

Narrow leafed lupines (*Lupinus angustofolius*) of the cultivar Gungurru, average weight 0.15 g were soaked for a day under tap water, with several changes of water and then allowed to sprout at a room temperature of approximately 25° C. for varying lengths of time (4-8 days).

All seeds were ground with a small quantity of sand in a mortar and pestle for about five minutes and stored in sealed beakers for varying lengths of time (65-88 minutes) before being extracted at pH 12 for 60-90 minutes, coarse filtered through a double layer of cloth, acidified at pH 3.5 and stored overnight before filtration through paper.

Results

The results are set out in Table 9 hereunder.

TABLE 9

| Sample | Age of seeds | Hydrolysis time | Alkaline extraction (pH/time) | Yield[A] (genisteins) | Yield[B] (genisteins) |
|---|---|---|---|---|---|
| A | 4 days | 80 minutes | 12/80 minutes | 42 mg | 26 0.20 |
| B | 5 days | 75 minutes | 12/90 minutes | 80 mg | 0.37 |
| C | 6 days | 67 minutes | 12/60 minutes | 98 mg | 0.45 |
| D | 7 days | 88 minutes | 12/75 minutes | 154 mg | 0.82 |
| E | 8 days | 65 minutes | 12/75 minutes | 144 mg | 0.99 |
| F | 9.5 days | 120 minutes | 12/330 minutes | 185 mg | 1.31 |

[A] genistein per 100 g of dried seed
[B] content in precipitate g/100 g

Example 3A

Soya bean seeds of an average dry weight of 0.16 g (0.15 g oven dried) were soaked for 11 hours excluding an air break of 1 hour after the first 7 hours. After being drained and left for 45 minutes the seeds were crushed and pounded well with added sand for about 5 minutes with a mortar and pestle and then stored in a beaker sealed against moisture loss at a room temperature of approximately 25° C.

After 80 minutes, the coarse paste was leached with alkaline solution adjusted to pH 12 for 2.5 hours before filtering, followed by adjustment of the filtered solution to pH 2.0. The acidified solution was allowed to settle over night at about 20° C. before being filtered through paper and dried, weighted portions were then leached with alcohol and the isoflavone solution levels checked.

Results

From 100 seeds obtained 7.27 g dried precipitate, about 0.15 g isoflavones per 100 g leachable with methanol, approximating to 70 mg of isoflavones/100 g of dried seeds.

Example 3B

Soya bean seeds were soaked for 24 hours with two 1 hour air breaks (at approximately 8 hours and 20 hours) and then soaked for approximately 1 hour every 12 hours thereafter. The seeds were ground with a small quantity of sand in a mortar and pestle for 5-10 minutes and stored in sealed beakers for varying lengths of time before being extracted with alkaline solution, coarse filtered through a double layer of cloth, acidified and stored overnight before filtration through paper.

Results

Seeds soaked for 24 hours and maintained for 5 hours before grinding and waiting for 80 minutes, extracted by alkaline at pH 12 for 2 hours then acidified to pH 3.5 had the following yield:

From 100 seeds obtained 7.387 g dried precipitate, of about 0.15 g of isoflavones per 100 g, approximating to 73mg/ 100 g of dried seeds.

Seeds soaked for 24 hours and maintained for 1.5 days thereafter, were at the stage of the first being visible beneath the seed coat being a few mm long. After grinding and waiting for 110 minutes, the coarse paste was extracted by alkaline at pH 12 for 140 minutes, after filtering through cloth the filtrate was divided and two equivalent portions and acidified to pH 3.5 and 4.5 respectively. The yields were as follows:

With pH 3.5 obtained 4.30 g dried precipitate, of about 0.20 g isoflavones per 100 g, approximating to 118 mg/100 g of dried seeds.

With pH 4.5 obtained 4.84 g dried precipitate, of about 0.23 g isoflavones per 100 g, approximating to 144 mg/100 g of dried seeds.

Seeds soaked for 24 hours and maintained 4 days thereafter were at the stage of the cotyledon just emerging from the seed coat to the point where cotyledons are bend downwards with respect to the root and opening slightly. The seeds were crushed and pounded well with added sand for about 5 minutes with a mortar and pestle, then stored in a beaker sealed against moisture loss at a room temperature of approximately 25° C., after a period of 140 minutes, the coarse paste was then leached with alkaline solution adjusted to pH 12 for 150 minutes before filtering, followed by adjustment of the filtered solution to pH 3.5. The acidified solution was allowed to settle over night at about 20° C. before being filtered through paper and dried, weighted portions were then leached with alcohol and the isoflavone yields are set out hereunder.

From 60 seeds obtained 6.17 g dried precipitate of about 0.336 g isoflavones per 100 g or approximately 223mg/100 g of dried seed. The concentration in the methanol leachate was 1.25 g/100 g.

Another batch of soya seeds were soaked for two hours and then held for an hour and a half before grinding with a small quantity of sand in a mortar and pestle for ten minutes, and storing a covered beaker to two hours, extracted with alkaline solution at pH 12 for two hours, then cloth filtered and rinsed, acidified to pH 3.5 and stored overnight before filtration through paper and drying.

From 100 seeds obtained 5.88 g dried precipitate of about 0.20 g isoflavones per 100 g or approximately 80 mg/100 g of dried seeds.

Example 4

8 g of leaves from Peppermint (*Mentha piperita*) plants were pounded with sand and a small amount of added water with a mortar and pestle for 1.5 minutes, and the leaf paste so produced allowed to stand for 13 minutes to permit hydrolysis of the eriocitrin (eriodictyol-7-rhaminoside glycoside) present.

The leaf paste was then made up to approximately 150 mL mixed solution-suspension and the pH adjusted to pH 12.0, and the pH was maintained between pH 11.8 and 12.0 for 90 minutes. After this the mixture was filtered through a cloth, before being adjusted to pH 2.0. The acidified solution was left overnight to allow the precipitate formed to settle out before being filtered on paper the next day and dried.

Results

The dried precipitate weighted 0.372 g. The ethyl alcohol leachable eriodictyol was measured as approximately 2.5 g per 100 g of the dried precipitate. This calculates out as approximately 118 mg per 100 g of peppermint leaf material.

Example 5

Commercially supplied soaked chickpeas of the Kabuli subtype with roots of approximately 2.5 cm in length but no visible leaf sprouts above were purchased from a supermarket and stored in a refrigerator at approximately 5° C. and at various times batches were soaked and permitted to develop further including to the stage of proper sprouted seeding. These were tested by taking the seeds, crushing and pounding well with added sand for about 10 minutes with a mortar and pestle, then storing in beakers sealed against moisture loss at a room temperature of approximately 25 to 28° C., after a period of at least 1.25-3 hours, the coarse paste was leached with alkaline solution adjusted to pH 12 for at least one hour before filtering, followed by adjustment of the filtered solution to pH 3.5.

The acidified solution was allowed to settle over night at about 20° C. before being filtered through paper and dried, weighted portions were then leached with alcohol and the isoflavone solution levels checked.

Results

Refrigerator stored sample with no extra soaking after purchase, seeds at the stage of no visible leaf sprouts but roots of up to 2.6 cm as measured from the bend as the root emerges from the seed, from 60 seeds obtained 9.15 g dried precipitate of about 0.08 g isoflavones per 100 g. The concentration in the methanol leachate was 0.6 g/100 g.

Seeds of the stage of no visible leaf sprouts but roots of up to 4.4 cm, from 60 seeds obtained 8.94 g dried precipitate of about 0.39 g isoflavones per 100 g. The concentration in the methanol leachate was 3.0 g/100 g.

Seeds of the stage of the leaf sprouts emerging to being completely out, from 40 seeds obtained 6.17 g dried precipitate of about 0.36 g -isoflavones per 100 g. The concentration in the methanol leachate was 2.2 g/100 g.

Seeds of the stage where the sprout cotyledons are separated with a large gap between and the sprout is up to 1.2 cm long, and roots of up to or longer than 5 cm but with no side roots on chickpea sprout roots, from 67 seeds obtained 8.08 g dried precipitate of about 0.41 g of isoflavones per 100 g. The concentration in the methanol leachate was 2.4 g/100 g.

Seeds of the stage where cotyledons are completely opened up with sprouts of up to 2.5 cm long and roots up to 6.7 cm long with side roots of up to 1.4 cm long, from 61 seeds obtained, 8.41 g dried precipitate of about 0.67 g of isoflavones per 100 g.

When seeds from the batch where the seeds had reached the stage of the leaf sprouts emerging to being completely out, were processed with the extra steps of after the crushing and waiting interval, being heated to 60° C. for forty minutes and with centrifuging after filtration before acidification to pH 2.0, from 50 seeds obtained 2.61 g dried precipitate of about 0.75 g isoflavones per 100 g.

In the examples it is important to note that the alkaline pH extraction effect can not be a result of the hydroxide ions merely increasing the negative charge on the plant materials and so forcing the negatively charged ionised isoflavonoid aglycones into solution due to negative ion—negative ion repulsion. In that case merely holding the plant material at an elevated pH for a longer time would result in increased quantities of the isoflavonoids moving out into solution. Instead the leached amount is effectively time independent, the yield changing little when the leach time is increased from 5 minutes to 1 hour when leaching at pH 10, but does respond fast to a pH change, clover leaf material extracted at pH 9.5 and cloth filtered, when the cloth filtered solids are rinsed with pH 12 solution rather than pH 9.5, an operation taking about a couple of minutes the extraction yield increased by 27%.

It can be speculated that the raising of the pH not only causes the aglycone to become water soluble but enables it to move into solution either by altering the physical nature of the plant material—less physical entrapment by opening up of structures present, or by changing some aspect of the chemical environment perhaps by altering equilibriums which hold flavonoids in some attachment. The later mechanism may be an explanation of the greater yield found with the alkaline extraction than with the conventional organic solvent extraction.

Throughout the specification, unless the context requires otherwise, the word "comprise" or variations such as "comprises" or "comprising", will be understood to imply the inclusion of a stated integer or group of integers but not the exclusion of any other integer or group of integers.

The claims defining the invention are as follows:

1. A method of producing an enriched flavonoid aglycone extract from a plant or plant material containing a flavonoid glycoside and/or conjugate thereof consisting of the following steps:
    (i). enzymatically converting the plant or plant material, wherein the enzyme converts the flavonoid glycoside or conjugate thereof in the plant or plant material into the flavonoid aglycone;
    (ii). adjusting the pH to render the flavonoid aglycone soluble and removing the insoluble fraction; and
    (iii). adjusting the pH to render the soluble flavonoid aglycone relatively insoluble and forming an extract containing the same;
    wherein the plant material is selected from leaves, petals, sepals, flowers, petrioles, shoots, roots, stems, seeds, pods, tubers, bark, cambium, wood, galls, fruits, vegetables, herbs, ferns, sap, resins, skins, peels, fruit rinds, pomace, wine marc, grain hulls, straw, hay, oil seed cakes, or a combination thereof.

2. A method according to claim 1 wherein the flavonoid aglycone is rendered soluble by adjusting the pH to approximately 8.5-12.5.

3. A method according to claim 1 wherein the flavonoid aglycone is rendered soluble by adjusting the pH to approximately 9-12.

4. A method according to claim 1 wherein the flavonoid aglycone is rendered soluble by adjusting the pH to approximately 11-12.

5. A method according to claim 1 wherein the flavonoid aglycone is rendered soluble by adjusting the pH to at least approximately 8.5.

6. A method according to claim 1 wherein the flavonoid aglycone is rendered soluble by adjusting the pH to at least approximately 9.

7. A method according to claim 1 wherein the flavonoid aglycone is rendered soluble by adjusting the pH to at least approximately 9.6.

8. A method according to claim 1 wherein the flavonoid aglycone is rendered soluble by adjusting the pH to approximately 11 or 12.

9. A method according to claim 1 wherein aeration is minimized in step (ii) to inhibit breakdown of the flavonoids.

10. A method according to claim 1 wherein the adjustment of the pH in step (ii) is achieved by the addition of an alkali.

11. A method according to claim 10 wherein the alkali is sodium hydroxide, sodium acetate, potassium hydroxide, calcium hydroxide or ammonia gas.

12. A method according to claim 1 wherein the soluble fraction in step (ii) is removed by any one or a combination of settling, filtration and centrifugation.

13. A method according to claim 1 wherein the flavonoid aglycone is rendered insoluble by adjusting the pH to approximately 2-6.

14. A method according to claim 1 wherein the flavonoid aglycone is rendered insoluble by adjusting the pH to approximately 2-5.6.

15. A method according to claim 1 wherein the flavonoid aglycone is rendered insoluble by adjusting the pH to approximately 2-3.5.

16. A method according to claim 1 wherein the flavonoid aglycone is rendered insoluble by adjusting the pH to approximately 2, 3.5, 3.6, 5.3, or 5.6.

17. A method according to claim 1 wherein the adjustment of the pH in step (iii) is achieved by the addition of an acid.

18. A method according to claim 17 wherein the acid is hydrochloric acid, sulphuric acid, phosphoric acid, acetic acid, nitric acid, lactic acid, tartaric acid, citric acid or propionic acid.

19. A method according to claim 1 wherein the insoluble fraction in step (iii) is separated by one or more of settling, filtration, crystallization, co-crystallization, and centrifugation.

20. A method according to claim 1 wherein the flavonoid aglycone or flavonoid glycoside is selected from the group consisting of chalcones, dihydrochalones, aurones, flavanones, flavones, neoflavonoids, flavonols, dihydroflavonols, proanthocyanidins, flavans, flavan-3-ols, biflavonoids acacetin, apigenin, baicalein, catechin, chrysin, chrysoeriol, datiscetin, dihydrobinetin, dihydrokaempferol, diosmetin; catechin, epicatechin, eriodictyol, fisetin, fustin, galangin, hesperetin, isorhamnetin, kaempferol, luteolin, digitoflavone, morin, myricetin, naringenin, oroxylin A, poncirretin, quercetagetin, quercetin, robinetin, scutellarein, silybin, silidianin, silicristin, skullcapflavone II, tangeretin, wogonin and isoflavones.

21. A method according to claim 1 wherein the flavonoid is genistein, daidzein, formononetin, biochanin A, or pratensein.

22. A method according to claim 1 wherein the plant is genetically modified.

23. A method according to claim 1 wherein the plant is a legume.

24. A method according to claim 23 wherein the legume comprises lupin, soy, chickpeas, white sweet clover, lucerne, alfalfa, or Trifolium species.

25. A method according to claim 1 wherein the enzyme is glycosidase, β-glycosidase, β-galactosidase, β-glucoronidase, pectinase, hesperidinase, anthocyanase, rhamnodiastase, naringinase, or takadiastase.

26. A method according to claim 1 wherein the enzyme is exogenous and is added to plant or plant material.

27. A method according to claim 1 wherein a plurality of enzymes is used in a sequential manner.

28. A method according to claim 1, wherein enzymatically converting the plant or plant material is achieved by disrupting the cellular structure of the plant or plant material such that at least one enzyme contained therein that is capable of converting a flavonoid glycoside or conjugate thereof into a flavonoid aglycone contacts the flavonoid glycoside or conjugate thereof contained within the plant or plant material.

29. A method according to claim 28 wherein the cellular structure is disrupted by grinding, crushing, pounding or rolling, freezing and thawing, enzyme treatments, hemicellulases, cellulases, ultrasonics, drying, exposure to ultra violet light, pressure reduction or elevation, extrusion, sealed batch pressure applications, microbial digestion or ensilagation, exposure to oxidising chemicals, detergents, or any combination of the foregoing.

30. A method according to claim 1, wherein the plant or plant material comprises an intact cellular structure.

31. A method of producing an enriched flavonoid aglycone extract from a plant or plant material containing a flavonoid glycoside and/or conjugate thereof consisting of the following steps:
(i). enzymatically converting the plant or plant material, wherein the enzyme converts the flavonoid glycoside or conjugate thereof in the plant or plant material into the flavonoid aglycone;
(ii). adjusting the pH to render the flavonoid aglycone soluble and removing the insoluble fraction, wherein pH is adjusted under conditions that minimize or prevent aeration; and
(iii). adjusting the pH to render the soluble flavonoid aglycone relatively insoluble and forming an extract containing the same;
wherein the plant material is selected from leaves, petals, sepals, flowers, petrioles, shoots, roots, stems, seeds, pods, tubers, bark, cambium, wood, galls, fruits, vegetables, herbs, ferns, sap, resins, skins, peels, fruit rinds, pomace, wine marc, grain hulls, straw, hay, oil seed cakes, or a combination thereof.

32. A method of producing an enriched flavonoid aglycone extract from a plant or plant material containing a flavonoid glycoside and/or conjugate thereof consisting of the following steps:
(i). enzymatically converting the plant or plant material, wherein the enzyme converts the flavonoid glycoside or conjugate thereof in the plant or plant material into the flavonoid aglycone;
(ii). adjusting the pH to render the flavonoid aglycone soluble and removing the insoluble fraction; and
(iii). adjusting the pH to render the soluble flavonoid aglycone relatively insoluble and forming an extract containing the same;
wherein the plant or plant material comprises soaked seeds, germinated seeds, sprouted seeds, or a combination thereof.

33. A method of producing an enriched flavonoid aglycone extract from a plant of plant material containing a flavonoid glycoside and/or conjugate thereof consisting of the following steps:
(i). enzymatically converting the plant or plant material, wherein the enzyme converts the flavonoid glycoside or conjugate thereof in the plant or plant material into the flavonoid aglycone;
(ii). adjusting the pH to render the flavonoid aglycone soluble and removing the insoluble fraction; and
(iii). adjusting the pH to render the soluble flavonoid aglycone relatively insoluble;
(iv). separating the insoluble flavonoid aglycone to form an extract containing the same, wherein salt is optionally added to aid in the separation; and
(v). optionally concentrating the extract;
wherein the plant material is selected from leaves, petals, sepals, flowers, petrioles, shoots, roots, stems, seeds, pods, tubers, bark, cambium, wood, galls, fruits, vegetables, herbs, ferns, sap, resins, skins, peels, fruit rinds, pomace, wine marc, grain hulls, straw, hay, oil seed cakes, or a combination thereof.

34. A method according to claim 33, wherein concentrating the extract is by evaporation or partial freezing.

35. A method of producing an enriched flavonoid aglycone extract from a plant or plant material containing a flavonoid glycoside and/or conjugate thereof consisting of the following steps:
(i). pretreating the plant or plant material to promote the production of enzymes therein necessary to effect conversion of flavonoid glycosides and conjugates thereof to the flavonoid aglycone;
(ii). enzymatically converting the plant or plant material, wherein the enzyme converts the flavonoid glycoside or conjugate thereof in the plant or plant material into the flavonoid aglycone;
(iii). adjusting the pH to render the flavonoid aglycone soluble and removing the insoluble fraction; and
(iv). adjusting the pH to render the soluble flavonoid aglycone relativily insoluble and forming an extract containing the same;
wherein the plant or plant material is seeds.

36. A method according to claim 35, wherein pre-treatment is by soaking the seeds for a length of time sufficient to promote the production of the enzymes.

37. A method according to claim 35, wherein the seeds are soaked for approximately 10 days or less.

38. A method according to claim 35, wherein the seeds are soaked for approximately 0.5 to 10 days.

* * * * *